United States Patent
Badawi et al.

(10) Patent No.: US 9,557,281 B2
(45) Date of Patent: Jan. 31, 2017

(54) EXCISED SPECIMEN IMAGING USING A COMBINED PET AND MICRO CT SCANNER

(75) Inventors: Ramsey D. Badawi, Woodland, CA (US); Kai Yang, West Sacramento, CA (US)

(73) Assignee: The Regents of the University of California, Oakland, CA (US)

( * ) Notice: Subject to any disclaimer, the term of this patent is extended or adjusted under 35 U.S.C. 154(b) by 231 days.

(21) Appl. No.: 14/124,654

(22) PCT Filed: Jun. 11, 2012

(86) PCT No.: PCT/US2012/041945
§ 371 (c)(1),
(2), (4) Date: Feb. 28, 2014

(87) PCT Pub. No.: WO2012/171029
PCT Pub. Date: Dec. 13, 2012

(65) Prior Publication Data
US 2014/0198893 A1    Jul. 17, 2014

Related U.S. Application Data

(60) Provisional application No. 61/495,340, filed on Jun. 9, 2011.

(51) Int. Cl.
*G01N 23/04* (2006.01)
*A61B 6/03* (2006.01)
(Continued)

(52) U.S. Cl.
CPC ............ *G01N 23/046* (2013.01); *A61B 6/032* (2013.01); *A61B 6/037* (2013.01); *A61B 6/4258* (2013.01);
(Continued)

(58) Field of Classification Search
CPC ....... A61B 6/032; A61B 6/037; A61B 6/0407; A61B 6/4258; A61B 6/508; A61B 6/5235; G01N 2223/1016; G01N 2223/108; G01N 2223/6126; G01N 23/046; G01N 2223/419; G01T 1/161
See application file for complete search history.

(56) References Cited

U.S. PATENT DOCUMENTS 5,902,310 A  * 5/1999  Foerster ............. A61B 17/0644
                                                    606/142
6,399,951 B1    6/2002  Paulus et al.
(Continued)

OTHER PUBLICATIONS

Hall N.C., et al., "Combined approach of perioperative 18F-FDG PET/CT imaging and intraoperative 18F-FDG handheld gamma probe detection for tumor localization and verification of complete tumor resection in breast cancer," World J Surg Oncol 2007;5:143.*
(Continued)

*Primary Examiner* — Wyatt Stoffa
(74) *Attorney, Agent, or Firm* — Kilpatrick Townsend & Stockton LLP

(57) ABSTRACT

Embodiments of the present invention provide methods and apparatus for imaging a tissue specimen excised during surgery with a combined positron emission tomography (PET) and micro computed tomography (micro CT) scanner. The specimen is scanned with a CT imaging system of the combined PET and micro CT scanner. The specimen is also scanned with a PET imaging system of the combined PET and micro CT scanner. A PET image is constructed based on data acquired by the PET imaging system. A micro CT image is constructed based on data acquired by the micro CT imaging system. The micro CT image includes at least one visualization of a lesion marker.

17 Claims, 5 Drawing Sheets

(51) Int. Cl.
*A61B 6/00* (2006.01)
*G01T 1/161* (2006.01)
*A61B 6/04* (2006.01)

(52) U.S. Cl.
CPC .............. *A61B 6/508* (2013.01); *A61B 6/5235* (2013.01); *G01T 1/161* (2013.01); *A61B 6/0407* (2013.01); *G01N 2223/108* (2013.01); *G01N 2223/1016* (2013.01); *G01N 2223/419* (2013.01); *G01N 2223/6126* (2013.01)

(56) References Cited

U.S. PATENT DOCUMENTS

| | | | | |
|---|---|---|---|---|
| 6,448,559 | B1* | 9/2002 | Saoudi | G01T 1/1603 250/367 |
| 6,449,331 | B1 | 9/2002 | Nutt et al. | |
| 7,149,565 | B2 | 12/2006 | Kojima et al. | |
| 7,352,840 | B1* | 4/2008 | Nagarkar | A61B 6/032 250/363.02 |
| 7,486,766 | B1 | 2/2009 | Nagarkar et al. | |
| 7,854,705 | B2 | 12/2010 | Pawluczyk et al. | |
| 7,881,427 | B2 | 2/2011 | Kalender et al. | |
| 2001/0044576 | A1* | 11/2001 | Vining | G06T 7/0012 600/416 |
| 2002/0191736 | A1* | 12/2002 | Shiota | A61B 6/4085 378/4 |
| 2003/0058984 | A1 | 3/2003 | Susami et al. | |
| 2003/0128801 | A1* | 7/2003 | Eisenberg | A61B 6/4291 378/19 |
| 2004/0030263 | A1 | 2/2004 | Dubrul et al. | |
| 2005/0116878 | A1* | 6/2005 | Warnberg | A61B 6/02 345/1.1 |
| 2006/0113482 | A1* | 6/2006 | Pelizzari | A61N 5/1049 250/370.09 |
| 2007/0297575 | A1* | 12/2007 | Mostafavi | A61B 6/032 378/207 |
| 2009/0080600 | A1 | 3/2009 | Keller et al. | |
| 2010/0128956 | A1* | 5/2010 | Yamaya | G01T 1/1611 382/132 |
| 2011/0021888 | A1* | 1/2011 | Sing | A61B 5/0507 600/302 |
| 2011/0105896 | A1* | 5/2011 | Zagorchev | A61B 6/508 600/426 |
| 2011/0251480 | A1* | 10/2011 | Graves | A61B 5/055 600/411 |
| 2012/0035457 | A1* | 2/2012 | Subramaniam | A61B 5/05 600/409 |
| 2012/0068076 | A1* | 3/2012 | Daghighian | A61B 6/037 250/363.03 |
| 2014/0066754 | A1* | 3/2014 | Chi Sing | A61B 5/0507 600/424 |
| 2014/0228671 | A1* | 8/2014 | Subramaniam | A61B 5/05 600/409 |

OTHER PUBLICATIONS

Goertzen, A.L. 2003. "Development of a Combined microPET and microCT System for Mouse Imaging." Doctoral Dissertation, University of California, Los Angeles.*

Song, Y.S., et al., "A sub-millimeter resolution PET detector module using a multi-pixel photon counter array" Phys. Med. Biol. 55 (Apr. 2010) 2573-2587.*

Durkee et al.; "Reproducibility and Accuracy of Tumor Volume Measurement at MicroCT Colonography in Living Mice"; *Acad. Radiol.*; 15:334-341 (2008).

Goertzen, A.L. 2003. "Development of a Combined microPET and microCT System for Mouse Imaging," Doctoral Dissertation, University of California, Los Angeles. Available online at bic.mni.mcgill.ca/users/goertzen/ALGoertzen Dissertation.pdf.

Lage et al., Design and performance evaluation of a coplanar multimodality scanner for rodent imaging, published online at stacks.iop.org/PMB/54/5427, Aug. 21, 2009 (15 pages)

Langheinrich et al.; "Diagnostic value of ex-vivo three-dimensional micro-computed tomography imaging of primary nonhematopoietic human bone tumors: osteosarcoma versus chondrosarcoma"; *Acta Radiol.*; 49(8):940-948 (2008). Abstract only.

Shi et al.; "Validation of finite element models of liver tissue using micro-CT": *IEEE Transactions on Biomedical Engineering*; 55(3):978-984 (2008).

Wolthaus et al.; "Fusion of respiration-correlated PET and CT scans: correlated lung tumour motion in anatomical and functional scans"; *Phys. Med. Biol.*; 50:1569-1583 (2005).

The International Search Report and Written Opinon of PCT/US2012/041945, mailed Oct. 4, 2012.

* cited by examiner

EXCISED SPECIMEN IMAGING USING A COMBINED PET AND MICRO CT SCANNER

CROSS-REFERENCES TO RELATED APPLICATIONS

The present application claims priority to U.S. Patent Application No. 61/495,340, filed Jun. 9, 2011, which is hereby incorporated by reference, as if set forth in full in this document, for all purposes.

STATEMENT AS TO RIGHTS TO INVENTIONS MADE UNDER FEDERALLY SPONSORED RESEARCH AND DEVELOPMENT

This invention was made with Government support under Grant Nos. CA 129561 & EB002138, awarded by the National Institutes of Health. The Government has certain rights in this invention.

BACKGROUND

Surgical treatments including mastectomy and lumpectomy are applied to remove tumors from patients having breast cancer. Optimal outcomes require tumorous tissue to be surgically removed as completely as possible. To aid in removal of tumors, a radiologist may insert a clip in a breast duing biopsy to mark the tumor. A guide wire or multiple guide wires may be inserted into the breast to help the surgeon locate the targeted tumor during surgery. The clip can be used as a target for the wire.

To determine whether sufficient tissue has been removed, an excised specimen is examined to determine whether an adequate margin of cancer-free tissue is present at the surface of the specimen. Currently, a two-dimensional X-ray radiograph of a lumpectomy specimen is routinely used to evaluate the completeness of tumor removal. To obtain the radiograph, a tissue specimen is compressed between X-ray plates and imaged. The radiograph may be used to detect calcifications at the borders of the specimen. The radiograph can also be used to detect wires and/or clips to determine whether these markers were removed during surgery. However, as both wires and clips can move during surgery, detection of these lesion markers provides insufficient information for accurate assesment of whether sufficient tissue was removed. Further, the two-dimensional nature of X-ray radiography and the compression required impede accurate identification of which margins of the specimen are clear of cancerous tissue. Accordingly, after the operation is complete, the removed specimen is subjected to histopathology for a more accurate determination of whether sufficient tissue was removed during surgery. Histopathology results often require several days to obtain due to the time required for specimen logging, grossing, preservation, paraffinization, cutting, staining, and microscopic review. Histophathology demonstrates positive margins necessitating reoperation in approximately 20-40% of patients treated with lumpectomy. The need for breast cancer patients to undergo a second surgery (and, potentially, additional subsequent surgeries) creates significant emotional and financial stress.

BRIEF SUMMARY

The present disclosure relates generally to a tissue specimen imager for locating positive margins in tissue specimens during surgery. Specifically, the tissue specimen imager uses positron emission tomography (PET) and micro computed tomography (micro CT) components to image a tissue specimen.

Embodiments of the present invention provide methods and apparatus for imaging a tissue specimen excised during surgery with a combined positron emission tomography (PET) and micro computed tomography (micro CT) scanner. The specimen is scanned with a CT imaging system of the combined PET and micro CT scanner. The specimen is also scanned with a PET imaging system of the combined PET and micro CT scanner. A PET image is constructed based on data acquired by the PET imaging system. A micro CT image is constructed based on data acquired by the micro CT imaging system. The micro CT image includes at least one visualization of a lesion marker.

Another aspect of the present invention relates to a system for imaging a surgically excised tissue specimen. The system includes a gantry. The system also includes a micro CT imaging system including an X-ray source coupled to the gantry and an X-ray detector coupled to the gantry. The system further includes a PET imaging system including at least two PET detector modules coupled to the gantry. A processor communicatively coupled to the PET imaging system and the micro CT imaging system is configured to receive PET data acquired by the PET imaging system, construct a PET image based on the received PET data, receive micro CT data acquired by the micro CT imaging system, and construct a micro CT image based on the received micro CT data. The micro CT image includes at least one visualization of a lesion marker.

To better understand the nature and advantages of the present invention, reference should be made to the following description and the accompanying figures. It is to be understood, however, that each of the figures is provided for the purpose of illustration only and is not intended as a definition of the limits of the scope of the present invention.

DETAILED DESCRIPTION

Figure 1:
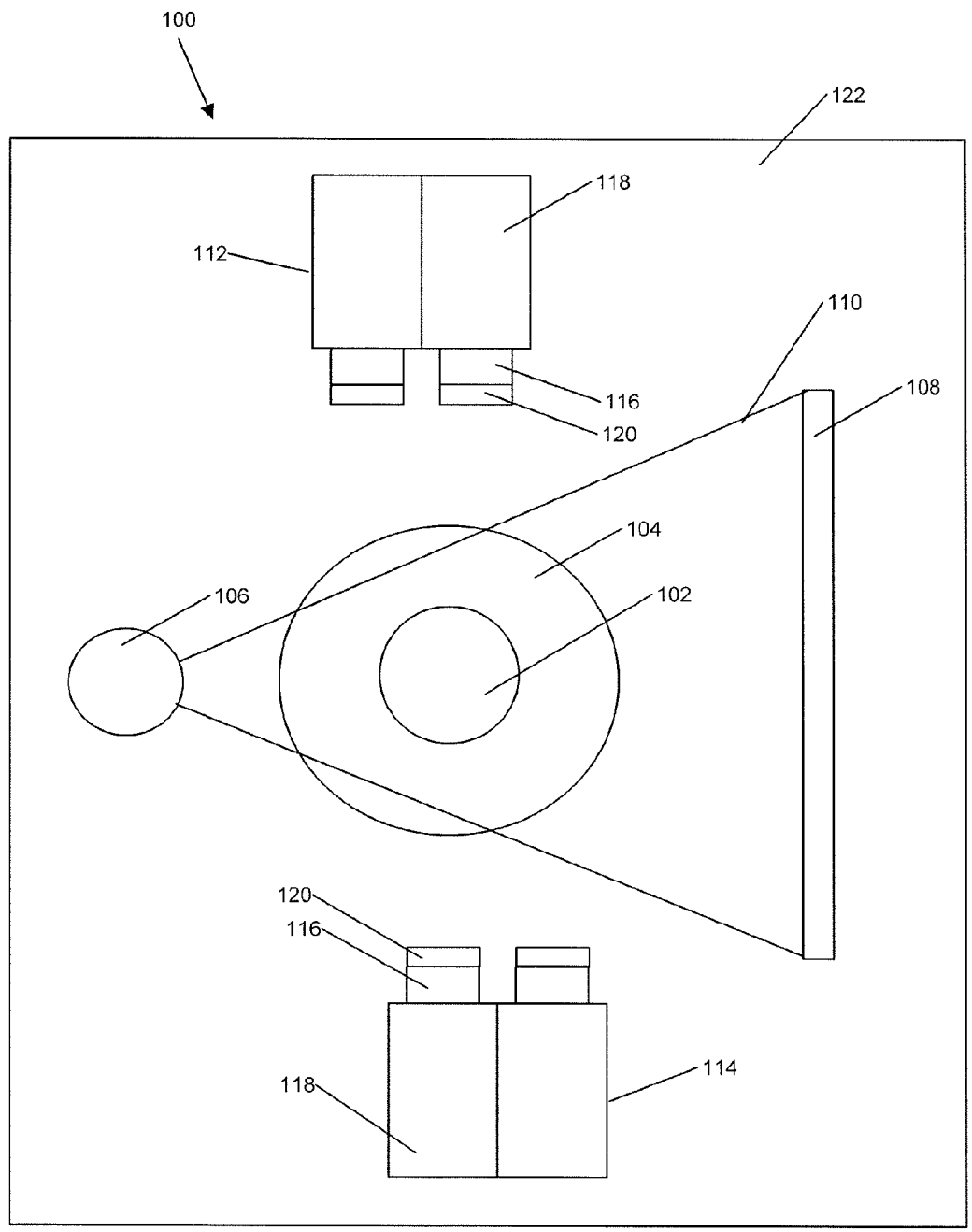
FIG. 1 is a system diagram showing an illustrative arrangement of elements of a combined PET and micro CT scanner according to an embodiment of the present invention.

Embodiments of the present invention relate to imaging a tissue specimen using a combined positron emission tomography (PET) and micro computed tomography (micro CT) scanner. A PET imaging system and a micro CT imaging system can be mounted to a gantry. Typically, the gantry is sufficiently compact to be mounted on a cart that can be used in used in or adjacent to an operating room.

An image constructued based on data acquired from the micro CT imaging system can show calcificaitons and lesion markers in the tissue specimen. Lesion markers such as clips and/or guide wires inserted into the body prior to surgery can help a surgeon locate a lesion (e.g., tumor) during surgery. If lesion markers that were inserted are not present in a tissue sample removed, this may be an indicator that the surgeon will need to remove additional tissue. The presence of calcifications or cancerous tissue close to the surface (i.e. in the margin) of the specimen are also potential indicators that removal of more tissue will be needed. For example, if cancerous tissue is at a depth of one millimeter below the surface of the specimen, it may be necessary to remove additional tissue to avoid leaving cancerous tissue in the body.

An image constructed based on data acquired from a PET system can show a cancerous tissue within a specimen. Preferably, a high resolution PET system is used. Whole body PET typically has a spacial resolution of four to five millimeters, which may be insufficient to determine whether the margin of a specimen (e.g., the part of the specimen from the surface to a depth of two millimeters below the surface of the specimen) is clear of cancerous tissue. A high resolution PET system (having, e.g., a sub-millimeter spatial resolution) may have sufficient resolution to support a determination that no cancerous tissue is present in the margin.

The combined PET and micro CT scanner allows a determination to be made during the surgery regarding whether sufficient tissue was removed. If additional removal is necessary, the surgeon can complete the excision prior to the patient leaving the operating room.

In a computed tomography (CT) imaging system, a specimen is positioned between an X-ray source and an X-ray detector. The X-ray source and X-ray detector may be rotated, e.g., by 0-720° relative to the specimen (such as by 360° relative to the specimen), to allow a series of cross sectional images of the specimen to be constructed based on the data acquired by the X-ray detector. In some embodiments, a three dimensional image may be constructed based on the data acquired by the X-ray detector. The specimen may be placed on a rotating specimen stage, such that the specimen is rotated relative to the X-ray source and X-ray detector. Alternatively, the X-ray source and X-ray detector may be mounted on a rotating gantry.

In a micro CT imaging system, the pixel sizes of the cross sectional images can be in the micrometer range. A micro CT imaging system is typically a smaller system compared with a whole-body CT system and may be used to obtain images of smaller objects. A micro CT imaging module can include an X-ray tube and and X-ray detector.

A positron emission tomography (PET) imaging system detects pairs of annihilation photons emitted by a positron-emitting radionuclide (tracer). The PET imaging system can include one or more pairs of PET detector modules. A specimen may be positioned between a pair of PET detector modules. Each PET detector module can include an array of scintillating crystals. In some embodiments, non-scintillating PET detectors can be used. At least one end of the array of scintillating crystals is coupled to a photodetector, such as a position sensing photomultiplier tube (PSPMT) or a position sensitive avalanche photodiode (PSAPD) Other photodetector technologies, such as silicon photomultipliers, may also be employed. In some embodiments, a PSAPD is coupled to the end of the array of scintillating crystals that faces a specimen and a PSPMT is coupled to the end of the array of scintillating crystals that is not facing the specimen.

Prior to PET imaging, a radioactive tracer isotope, such as fluorodeoxyglucose (FDG), is injected into a patient. After the FDG has circulated through the patient's body, a specimen is surgically excised from the patient's body. FDG is a glucose analog that is internalized more rapidly by cancer cells than by normal cells. As the FDG travels through the patient's circulatory system, the FDG adheres to or is taken up by cancer cells. The high level of radioactivity of the cancer cells in comparison with non-cancerous tissue allows visualization of the cancer cells in a PET image. As the tracer isotope decays, it emits a positron. When the positron interacts with an electron, a pair of annihilation photons are produced, moving in opposite directions. The two photons can be detected by two PET detector modules located across from each other with respect to a specimen. When the two photons reach scintillator crystals of the two PET detector modules, the crystals can absorb the energy of the photons and emit the energy as light. Photodetectors attached to the scynicallator crystals can determine the position and time of arrival of the photon based on the light emitted by the scintillator crystal. If two photodetectors of the two PET detector modules detect corresponding photon arrivals within a particular time frame, the photons are determined to originate from the same cancer cell. Mathematical construction (e.g, maximum a posteriori (MAP) reconstruction) can be used to construct an image based on the distribution of activity detected by the PET detector modules. Two-dimensional or three-dimensional images may be constructed from the data acquired by the PET imaging system.

A combined PET and micro CT scanner may have a PET imaging system including two or more PET detector modules connected to a gantry and a micro CT imaging system including one or more micro CT imaging modules connected to the gantry. Data may be sequentially or simultaneously acquired from the PET imaging system and the micro CT imaging system. PET images constructed from data acquired by the PET imaging system and micro CT images acquired from the micro CT imaging system may be combined into a single superposed image. The combined PET and micro CT scanner is described further below with reference to FIG. 1.

FIG. 1 is a system diagram showing a top down view of an illustrative arrangement of elements of a combined PET and micro CT detector 100 according to an embodiment of the present invention. Surgically excised specimen 102 can be loaded onto specimen stage 104. In some embodiments, specimen stage 104 is a rotatable specimen stage. Combined PET and micro CT scanner 100 can include specimen stage 104, X-ray source 106, X-ray detector 108, PET detector 112 and PET detector 114 may be mounted to a gantry 122. The elements of combined PET and micro CT scanner 100 may alternatively be mounted to a cart, table, slab or other surface. In some embodiments, one or more elements of combined PET and micro CT scanner 100 are movably attached to a gantry 122 or a surface.

A micro CT imaging system can include X-ray source 106 and X-ray detector 108. X-ray source 106 may be an X-ray tube having a 1-100 μm (e.g., 70 μm) focal spot (such as XTF5011, Oxford Instruments, Scotts Valley, Calif., capable of 4-50 kVp and 0-1.0 mA operation). X-ray detector 108 may be a CMOS detector. (An exemplary CMOS detector is Shad-o-Box 2048, Rad-icon Imaging Corp., Santa Clara, Calif., having an active area of 50×100 $mm^2$ and pixel size of 48×48 $\mu m^2$.) In some embodiments, a CCD detector may be used for X-ray detector 108. X-ray 110 emitted from X-ray source 106 is cast on specimen 102 and is detected at X-ray detector 108.

A PET imaging system can include PET detector modules 112 and 114. Specimen 102 is located between PET detector modules 112 and 114, which are positioned opposite from each other with respect to specimen 102. PET detector modules 112 and 114 each include scintillating crystals array 116. Scintillating crystals array 116 may be, for example, an array of lutetium orthosilicate (LSO) crystals. In an exemplary embodiment, a 36×36 array of 0.44×0.44×8.0 mm³ LSO crystals is used, each crystal polished on at least one side and coated by a specular reflective material (e.g., VM 2000) to enhance light output. In another embodiment, crystals may be unpolished and separated with a 50 μm layer of white paper reflector giving the array a crystal pitch of 0.5 mm. Other crystal types and configurations may be used.

A position sensitive avalanche photodiode (PSAPD) 120 may be coupled to the end of scintillating crystals array 116 that faces specimen 102. PSAPD 120 may be, for example, a PSAPD having an active area of 20×20 mm² (e.g., by Radiation Monitoring Devices, Inc.). A position sensitive photomultiplier tube (PSPMT) 118 is coupled to the end of scintillating crystals array 116 that does not face specimen 102. (PSPMT 118 may be, e.g., Hamamatsu M64). The output of the PSPMT can be multiplexed using a resistive network into 4 outputs (2 for X and 2 for Y positioning). Photodetectors 120 (e.g., PSAPD) and 118 (e.g., PSPMT) can determine the x/y position of the gamma ray interactions with scintillation crystal 116. In some embodiments, scintillation crystal array 116 may be coupled to photodetectors with a light guide. The PET detector may have a spatial resolution of 3.0 mm or less, such as a spatial resolution of less than 1.5 mm, e.g., a spatial resolution of less than 1.0 mm. In some embodiments, an X-ray shield is placed between x-ray source 106 and PET detectors 112 and 114. The x-ray shield can protect PET detectors 112 and 114 from x-rays arising directly or indirectly from the X-ray source.

PET detectors may achieve high resolution by having arrays with small elements (e.g., half a millimeter or less in size). Thick arrays may receive more photons, resulting in better data quality. However, as arrays grow thicker, spatial resolution is diminished. A dual ended approach in which the PET detector has photodetector 120 (e.g., PSAPD) and photodetector 118 (e.g., PSPMT) attached to opposite ends of scintillating crystal 116 can reduce the loss of resolution resulting from thick arrays. This is because a dual ended readout approach can allow depth of interaction encoding (providing a z-position of the annihilation photon interaction in scintillating crystal 116.)

PET detectors 112 and 114 may be positioned off center with respect to the specimen stage 104 to produce a larger field of view. In some embodiments, PET detectors 112 and 114 are movably mounted to gantry 122. For example, PET detectors 12 and 114 may be horizontally and/or vertically translatable to allow imaging of large specimens. In some embodiments, the PET imaging system and/or CT imaging system can be rotatable with respect to specimen stage 104.

Figure 2:
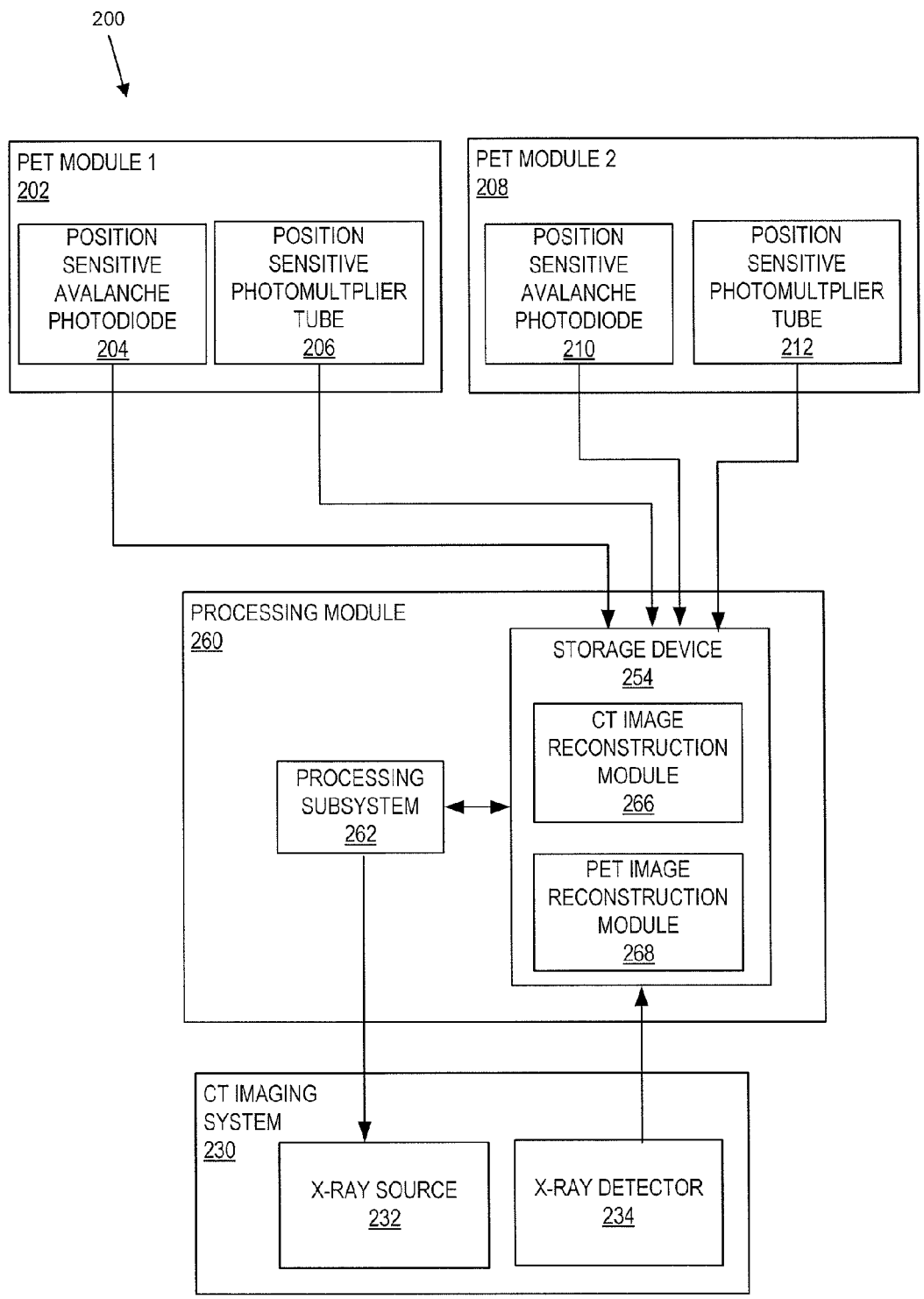
FIG. 2 is a block diagram of the combined PET and micro CT scanner according to an embodiment of the present invention.

FIG. 2 is a block diagram of a system 200, which can be, e.g., an implementation of the devices shown in FIG. 1. System 200 includes PET detector modules 202 and 208 (e.g., implementing PET detector modules 112 and 114 of FIG. 1), CT imaging system 230 including X-ray source 232 and X-ray detector 234 (e.g., implementing X-ray source 106 and X-ray detector 108 of FIG. 1) and processing module 260 according to an embodiment of the present invention.

Processing module 260 can provide computing capability. Processing module 260 can include processing subsystem 262 and storage device 254. Processing system 262 can control X-ray source 232. For example, processing subsystem 262 can transmit instructions and/or power to X-ray source 232 to initiate production of x-rays from x-ray source 232 and to terminate production of X-rays. In some embodiments, processing subsystem can be configured to receive data from PSAPD 204, PSPMT 206, PSAPD 210, PSPMT 212, and X-ray detector 234. Processing module device 260 can also include other components (not explicitly shown) such as a power supply, user interface (e.g., input devices such as a keyboard, output devices such a display), network interface, and other components operable to provide various enhanced capabilities.

Storage device 254 can be implemented, e.g., using disk, flash memory, or any other non-transitory storage medium, or a combination of media, and can include volatile and/or non-volatile media. In some embodiments, storage device 254 can receive and/or store data such as data acquired by one or more of PSAPD 204, PSPMT 206, PSAPD 210, PSPMT 212, and X-ray detector 234. In some embodiments, storage device 254 can also store sets of instructions to be executed by processing subsystem 262 including CT image reconstruction module 266 and PET image reconstruction module 268. CT image reconstruction module 266 can construct images based on data acquired by X-ray detector 234. PET image reconstruction module 268 can construct images based on data acquired by one or more of PSAPD 204, PSPMT 206, PSAPD 210, and PSPMT 212. In some embodiments, storage device 254 may store a set of instructions to be executed by processing subsystem 262 for constructing a combined image based on data received by PET modules 202 and 208 and CT imaging system 230.

Typically, communications between components of system 200 occur via wired connections, but wireless connections may be used. Further, while the portable device and accessory are described herein with reference to particular blocks, it is to be understood that these blocks are defined for convenience of description and are not intended to imply a particular physical arrangement of component parts. Further, the blocks need not correspond to physically distinct components. Blocks can be configured to perform various operations, e.g., by programming a processor or providing appropriate control circuitry, and various blocks might or might not be reconfigurable depending on how the initial configuration is obtained. Embodiments of the present invention can be realized in a variety of apparatus including electronic devices implemented using any combination of circuitry and software.

Figure 3:
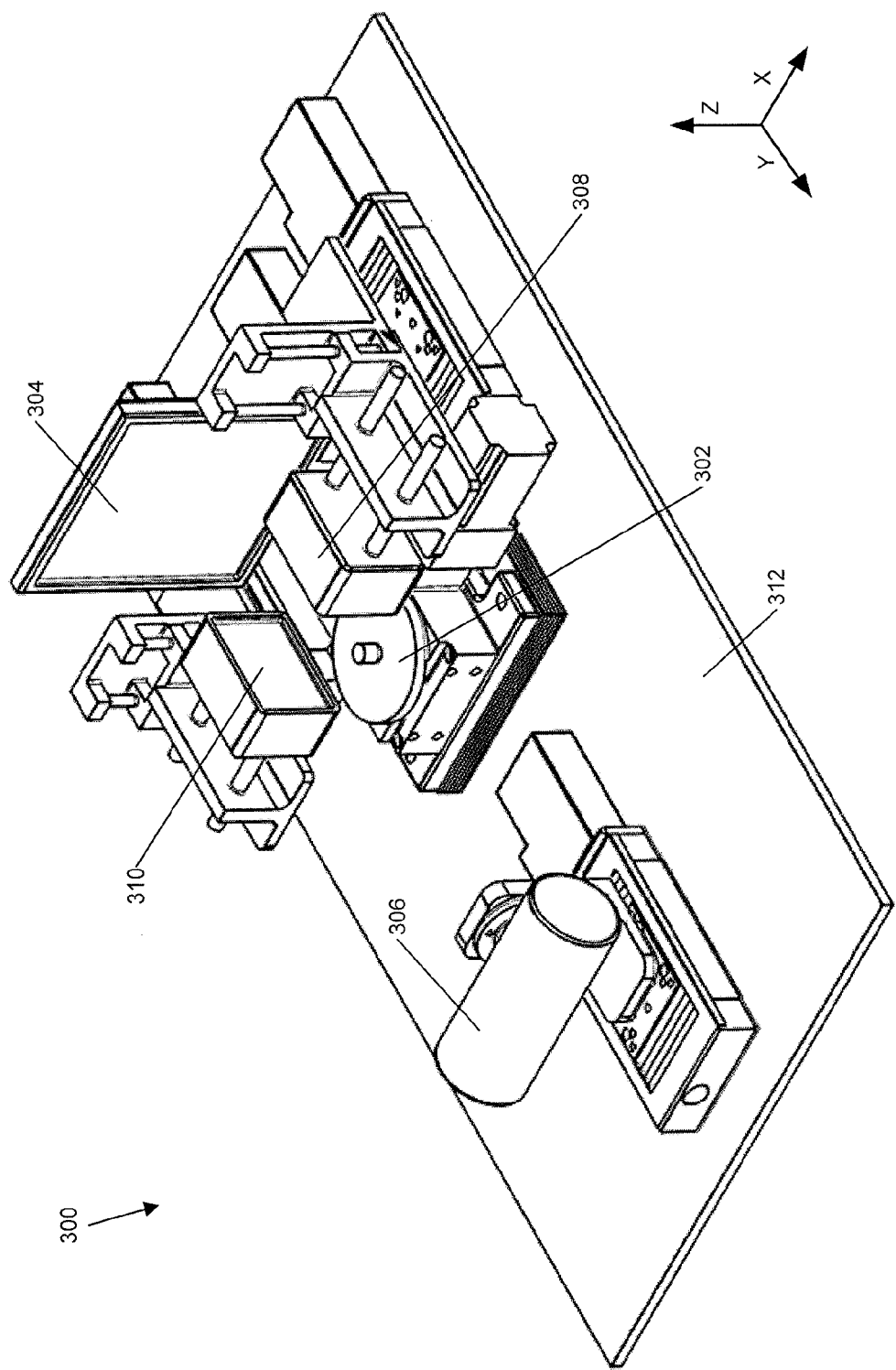
FIG. 3 is a perspective diagram of the combined PET and micro CT scanner according to an embodiment of the present invention.

FIG. 3 is a perspective diagram depicting an exemplary combined PET and micro CT scanner 300 (which can be, e.g., an implementation of the devices shown in FIG. 1) in accordance with an embodiment. A surgically excised sample can be mounted on rotatable specimen stage 302. Specimen stage 302 can rotate (e.g., by 360°) to allow imaging of the specimen by X-ray detector 304, which is configured to receive the X-rays emitted by X-ray source 306. In some embodiments, one or more of PET detector modules 308 and 310, X-ray detector 304 and X-ray source 306 can rotate around specimen stage 302. Specimen stage 302 can also translate in the Z direction to allow imaging of a large sample.

The magnification of the image produced by CT imaging system including X-ray detector 304 and X-ray source 306 can be adjusted by translation of one or both of 304 and 306 along the Y axis. X-ray detector 304 and X-ray source 306 can also be translated along the X and Z axes. PET detector modules 308 and 310 can be translated along the X, Y and Z axes to provide expanded coverage of large specimens.

Rotatable specimen stage 302, X-ray detector 304, X-ray source 306, and PET detector modules 308 and 310 can be connected to gantry 312.

Figure 4:
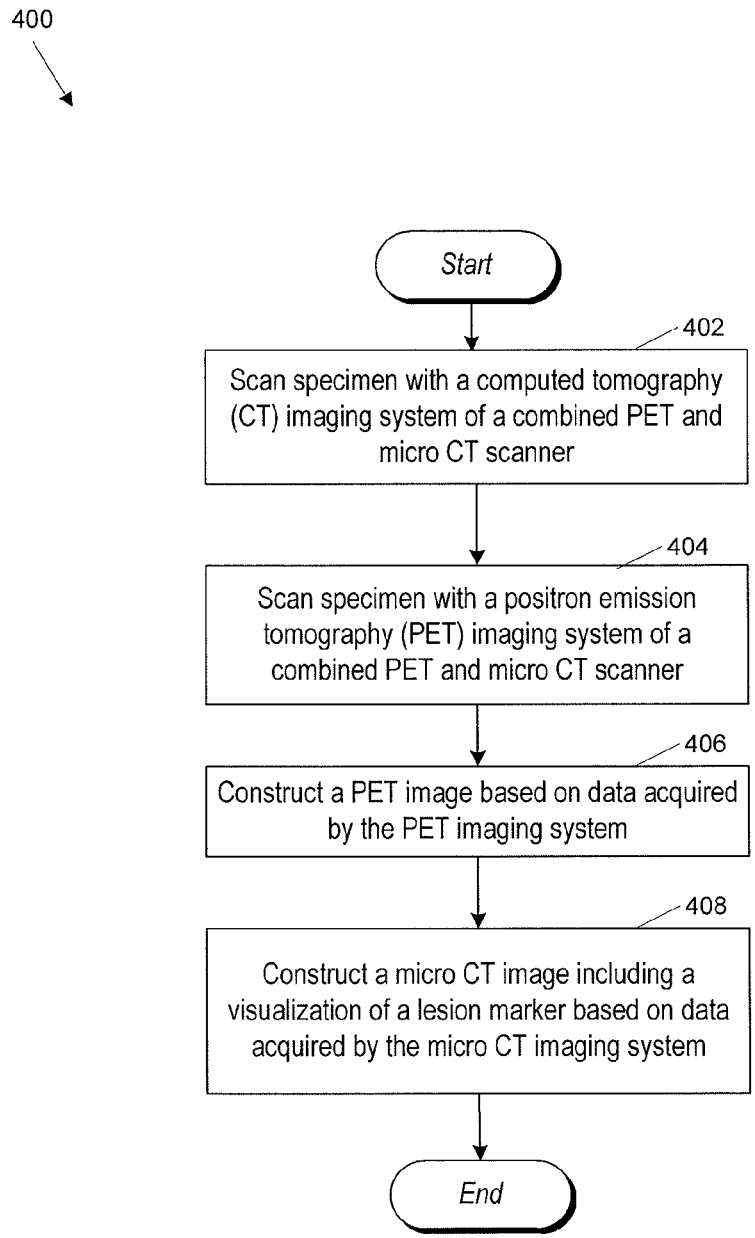
FIG. 4 is a flow diagram of a process for imaging a tissue specimen excised during surgery.

FIG. 4 is a flow diagram of a process 400 for imaging a tissue specimen excised during surgery. At block 402, a surgically excised specimen is scanned with a micro CT imaging system of a combined PET and micro CT scanner (e.g., system 100 described with reference to FIG. 1).

At block 404, the surgically excised specimen is scanned with a PET imaging system of the combined PET and micro CT scanner, At block 406, a PET image is constructed based on data acquired by the PET imaging system. At block 408, a micro CT image is constructed based on data acquired by the micro CT imaging system. The micro CT image includes at least one visualization of a lesion marker (e.g., a guide wire or clip).

The scans occurring in blocks 402 and 404 may occur in any order, or simultaneously. Further, the image construction occurring in blocks 406 and 408 may occur in any order, or simultaneously. In some embodiments, an image based on data acquired by the PET imaging system and data acquired by the CT imaging system is constructed.

Figure 5:
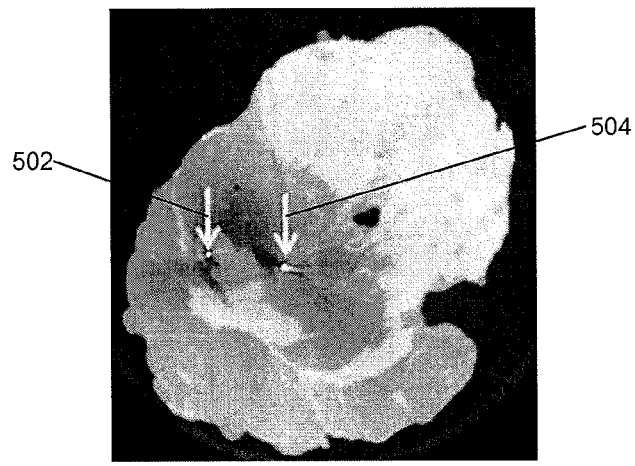
FIG. 5 shows an image of a surgically excised specimen constructed from data acquired by a micro CT imaging system.

FIG. 5 shows an image of a surgically excised specimen constructed from data acquired by a micro CT imaging system. A biopsy clip is visible as a relatively lighter area indicated by an arrow at 502 and a guide wire is visible as the relatively lighter area indicated by an arrow at 504.

Figure 6:
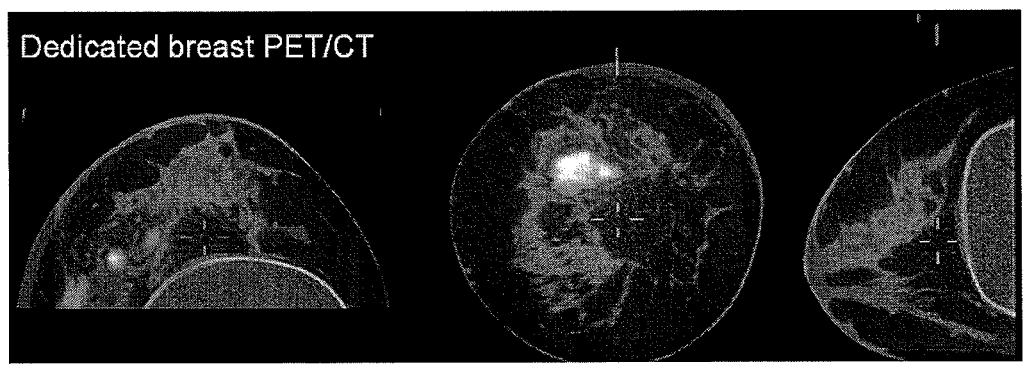
FIG. 6 shows an image of breast based on data acquired by a combined PET and CT scanner.

FIG. 6 shows an image of breast having palpable, mammographically evident disease. The image is based on data acquired by a combined PET and CT scanner. The PET imaging system used to create the image included two PET detector modules each having 1036 3 mm×3 mm scintillating crystal elements which rotate around the field of view.

Embodiments of the present invention can be realized using any combination of dedicated components and/or programmable processors and/or other programmable devices. The various processes described herein can be implemented on the same processor or different processors in any combination. Accordingly, where components are described as being configured to perform certain operations, such configuration can be accomplished, e.g., by designing electronic circuits to perform the operation, by programming programmable electronic circuits (such as microprocessors) to perform the operation, or any combination thereof. Processes can communicate using a variety of techniques including but not limited to conventional techniques for interprocess communication, and different pairs of processes may use different techniques, or the same pair of processes may use different techniques at different times. Further, while the embodiments described above may make reference to specific hardware and software components, those skilled in the art will appreciate that different combinations of hardware and/or software components may also be used and that particular operations described as being implemented in hardware might also be implemented in software or vice versa.

Computer programs incorporating various features of the present invention may be encoded on various computer readable storage media; suitable media include magnetic disk or tape, optical storage media such as compact disk (CD) or DVD (digital versatile disk), flash memory, and the like. Computer readable media encoded with the program code may be packaged with a compatible electronic device, or the program code may be provided separately from electronic devices (e.g., via Internet download).

While the invention has been described with respect to specific embodiments, one skilled in the art will recognize that numerous modifications are possible. Thus, although the invention has been described with respect to specific embodiments, it will be appreciated that the invention is intended to cover all modifications and equivalents within the scope of the following claims.

What is claimed is:

1. A method for imaging a tissue specimen excised during surgery, the method comprising, by a combined positron emission tomography (PET) and micro computed tomography (micro CT) scanner:
   scanning the surgically excised tissue specimen placed on a specimen stage with a computed tomography (CT) imaging system of the combined PET and micro CT scanner, the combined PET and micro CT scanner including an X-ray tube, an X-ray detector and at least one PET detector module, wherein each one of the X-ray tube, the X-ray detector and the at least one PET detector module are translatable along X, Y and Z axes relative to the specimen stage;
   scanning the surgically excised tissue specimen placed on the specimen stage with a positron emission tomography (PET) imaging system of the combined PET and micro CT scanner;
   constructing a PET image of the surgically excised tissue specimen based on data acquired by the PET imaging system; and constructing, during the surgery, a three-dimensional micro CT image of the surgically excised tissue specimen based on data acquired by the micro CT imaging system, wherein the three dimensional micro CT image includes at least one visualization of a lesion marker and illustrates tissue structure of a margin of the surgically excised tissue specimen.

2. The method of claim 1, wherein the PET imaging system has spatial resolution of less than 1.5 mm.

3. The method of claim 1, wherein the PET imaging system has a spatial resolution of less than 1.0 mm.

4. The method of claim 1, wherein the at least one PET detector module of a PET imaging system comprises:
   an array of scintillating crystals;
   a position sensitive avalanche photodiode coupled to a first face of the array that faces the specimen;
   a position sensing photomultiplier tube coupled to a second face of the array opposite the first face of the array.

5. The method of claim 1, wherein the distance between the X-ray tube and the X-ray detector is adjustable.

6. The method of claim 1, wherein the lesion marker is a guide wire.

7. The method of claim 1, wherein the lesion marker is a clip.

8. A system for imaging a tissue specimen excised during surgery, the system comprising:
   a gantry;
   a micro computed tomography (micro CT) imaging system including an X-ray source coupled to the gantry and an X-ray detector coupled to the gantry;
   a positron emission tomography (PET) imaging system including at least two PET detector modules coupled to the gantry, wherein each one of the X-ray source, the X-ray detector and at least one of the PET detector modules are translatable along X, Y and Z axes relative to the gantry; and
   a processor communicatively coupled to the PET imaging system and the micro CT imaging system, the processor configured to:
   receive PET data acquired by the PET imaging system;

construct a PET image of a surgically excised tissue specimen based on the received PET data;

receive micro CT data acquired by the micro CT imaging system; and construct, during the surgery, a three dimensional micro CT image of the surgically excised tissue specimen based on the received micro CT data, wherein the three dimensional micro CT image of the surgically excised tissue specimen includes at least one visualization of a lesion marker and illustrates tissue structure of a margin of the surgically excised tissue specimen.

9. The system of claim 8, wherein the PET imaging system has spatial resolution of less than 1.5 mm.

10. The system of claim 8, wherein the PET imaging system has a spatial resolution of less than 1.0 mm.

11. The system of claim 8, wherein the at least one PET detector module comprises an array of scintillating crystals and at least one end of the array is coupled to a photodetector.

12. The system of claim 8, further comprising a specimen stage coupled to the gantry, wherein the at least two PET detector modules are positioned off center with respect to the specimen stage.

13. The system of claim 8, wherein the at least one PET detector module of the PET imaging system comprises:

an array of scintillating crystals; a position sensitive avalanche photodiode coupled to a first face of the array that faces the specimen;

a position sensing photomultiplier tube coupled to a second face of the array opposite the first face of the array.

14. The system of claim 8, further comprising a specimen stage coupled to the gantry, wherein the specimen stage is configured to be rotatable.

15. The system of claim 14, wherein the specimen stage is configured to be vertically translatable.

16. The system of claim 8, wherein the micro CT imaging system further includes a second X-ray tube that is coupled to the gantry and a second X-ray detector coupled to the gantry.

17. The system of claim 8, further comprising an X-ray shield disposed between the at least two PET detector modules and the X-ray source.

* * * * *